(12) United States Patent
Porter et al.

(10) Patent No.: US 9,341,578 B2
(45) Date of Patent: May 17, 2016

(54) LED-BASED INSPECTION OF A PAINTED SURFACE FINISH

(71) Applicant: GM GLOBAL TECHNOLOGY OPERATIONS LLC, Detroit, MI (US)

(72) Inventors: Patrick A. Porter, Howell, MI (US); Alexander K. Peat, Saline, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 0 days.

(21) Appl. No.: 14/506,714

(22) Filed: Oct. 6, 2014

(65) Prior Publication Data

US 2016/0097725 A1   Apr. 7, 2016

(51) Int. Cl.
*G01N 21/00* (2006.01)
*G01N 21/88* (2006.01)
*F21V 33/00* (2006.01)
*F21V 7/00* (2006.01)
*G01N 21/95* (2006.01)
*F21Y 103/00* (2016.01)
*F21W 131/402* (2006.01)

(52) U.S. Cl.
CPC .......... *G01N 21/8806* (2013.01); *F21V 7/0066* (2013.01); *F21V 33/00* (2013.01); *G01N 21/95* (2013.01); *F21W 2131/402* (2013.01); *F21Y 2103/003* (2013.01)

(58) Field of Classification Search
CPC .................... G01N 2035/00881; G01N 21/59; G01N 2021/6432; G01N 2021/7786; G01N 21/0303; G01N 21/51; G01N 21/6408; G01N 21/783; G01N 2333/575; G01N 2333/62; G01N 2333/91188; G01N 2333/96463; G01N 33/5431
See application file for complete search history.

(56) References Cited

U.S. PATENT DOCUMENTS

| | | | | |
|---|---|---|---|---|
| 5,367,378 A | * | 11/1994 | Harding | G01N 21/8806 356/613 |
| 5,636,024 A | * | 6/1997 | Crookham | G01M 11/005 354/237.1 |
| 5,911,500 A | * | 6/1999 | Barnett | G01N 21/8806 362/145 |
| 6,529,283 B1 | * | 3/2003 | Demopoulos | G01B 11/14 356/606 |

(Continued)

FOREIGN PATENT DOCUMENTS

JP    2007183225    *    7/2007

OTHER PUBLICATIONS

"Civlight's 300degree-angle T8 LED tube offers 90+ CRI and 100lm/W efficiency", Nov. 15, 2013, http:llwww.ledsmagazine.com/ugc/2013/11/civlight-s-300-angle-t8-led-tube-offers-90-cri-and-100lm-w-efficiency.html.

*Primary Examiner* — Michael P Stafira
(74) *Attorney, Agent, or Firm* — Quinn Law Group, PLLC

(57) ABSTRACT

A method of inspecting a painted finish of a component such as a vehicle body or panel includes positioning the component with respect to an array of LED lighting fixtures each having LED tubes and generating light via the array with a predetermined set of lighting characteristics. The set of lighting characteristics includes a striped pattern, a beam angle of at least 120 degrees, and a CRI of at least 85 or at least 90. The method includes inspecting the painted surface for defects while illuminating the component with the light from the array. A control action is executed with respect to the component when the component contains a threshold number and/or a threshold size of the defects. Each array may have two LED tubes and four angled reflectors, and illuminating includes reflecting light from the LED tubes off of the angled reflectors toward the painted surface.

7 Claims, 3 Drawing Sheets

(56) References Cited

U.S. PATENT DOCUMENTS

| | | | |
|---|---|---|---|
| 2004/0119980 A1* | 6/2004 | Ringler | G01N 21/57 356/445 |
| 2009/0268965 A1* | 10/2009 | Mita | G01B 11/25 382/190 |
| 2013/0057678 A1* | 3/2013 | Prior Carrillo | G01N 21/8806 348/125 |

* cited by examiner

LED-BASED INSPECTION OF A PAINTED SURFACE FINISH

TECHNICAL FIELD

The present disclosure relates to LED-based inspection of a painted finish.

BACKGROUND

Automotive bodies, panels, and other painted components are typically electro-coated prior to application of one or more coats of a pigmented primer. The primer coats are followed by a top coat. A final coat of transparent sealer is applied to the top coat to provide the final paint finish. The presence of dirt, oil, or other debris at any stage of the painting process can result in topographic defects in the surface finish. Various approaches exist for inspection of a painted surface finish to help detect such topographic defects. However, existing inspection processes and lighting standards may be less than optimal in terms of energy usage and defect detection efficiency.

SUMMARY

A light-emitting diode (LED)-based method is disclosed herein for inspecting a painted surface finish of a component, for instance an automotive body or a panel. The method is intended to improve upon existing manual inspection processes. Such processes typically surround a painted component with an array of fluorescent tubes. Light from the fluorescent tubes is reflected toward the component via polished, elongated parabolic reflectors. The parabolic reflectors illuminate the component with what is referred to in the art as a "zebra striped" lighting pattern, i.e., an image of six stripes of light providing alternating light and dark contrast. Detection of topographic defects in the painted surface finish of the component is facilitated by movement of defects into and out of the contrasting stripes of projected light. However, conventional fluorescent-based lighting fixtures remain less than optimal in terms of energy consumption and defect detection efficiency.

The present method of inspection uses LED tubes, for instance in the T5, T8, or T12 standard tube sizes, in existing or new lighting fixtures of the type described generally above. Multiple LED lighting fixtures are utilized. Each LED lighting fixture has a pair of LED tubes modified as set forth herein so as to illuminate the component having a painted finish with light according to a calibrated set of lighting parameters. The calibrated set of lighting parameters includes the projection of zebra striping as described above at a beam angle of at least 120 degrees, a color temperature of about 5000° K, and a color rendering index (CRI) of at least 90. In another embodiment, the beam angle is at least 210 degrees. The CRI may be in the range of 90-93 in yet another embodiment. The color temperature may be exactly 5000° K in other embodiments.

As is well known in the art, LED tubes are emerging as commercially available replacement options for fluorescent tubes. LED tubes and other LED lighting devices enjoy energy efficiencies of about 90 percent and do not present the disposal concerns of fluorescent devices. Additionally, LED tubes typically enjoy a longer useful life relative to conventional fluorescent tubes. All of this leads to reduced energy consumption, lower maintenance costs, lower carbon footprints, and reduced landfill costs, in spite of the higher initial cost of an LED tube.

However, conventional off-the-shelf LED tubes include board-mounted LEDs aligned with a plane of the circuit board driving the LEDs. Such LEDs typically produce a beam angle of 65-120 degrees, with the term "beam angle" referring to the degree of width of any light emanating from the light source, i.e., the angle between points on opposite sides of a beam axis where the light intensity drops to 50% of its maximum value. Conventional LED tubes have a relatively low CRI of about 80. It is therefore recognized herein that off-the-shelf LED tubes, even if some may comply with individual specifications as set forth herein, may not meet the combined specified beam angle, CRI, and color temperature lighting requirements for the effective manual inspection of painted surfaces according to the present method.

The method according to an example embodiment includes positioning a component having a painted surface with respect to an array of LED lighting fixtures and then illuminating the painted surface with striped light from the array. Illuminating the painted surface may include irradiating the painted surface with a striped pattern of the light at a beam angle of at least 120 degrees and a CRI of at least 90, with the striped pattern being in one embodiment exactly six stripes of the light per lighting fixture. For instance, light from two LED tubes per fixture may be reflected from a parabolic, elongated reflector to generate the six stripes of light. In another embodiment, the beam angle is at least 210 degrees. The CRI may be in the range of 90-93 in another embodiment. The color temperature of the light may be about 5000 degrees Kelvin (° K), i.e., ±500° K, which is recognized herein as well suited to the inspection of painted surfaces and an improvement over existing fluorescent-based methods.

The method further includes inspecting the painted surface for topographic defects while illuminating the component with the light from the array. A first control action is executed if the component contains less than a threshold number and/or size of the topographic defects. A second control action is executed if the component contains more than a threshold number and/or size of the topographic defects.

The above and other features and advantages are readily apparent from the following detailed description of the best modes for carrying out the disclosure when taken in connection with the accompanying drawings.

DETAILED DESCRIPTION

Figure 1:
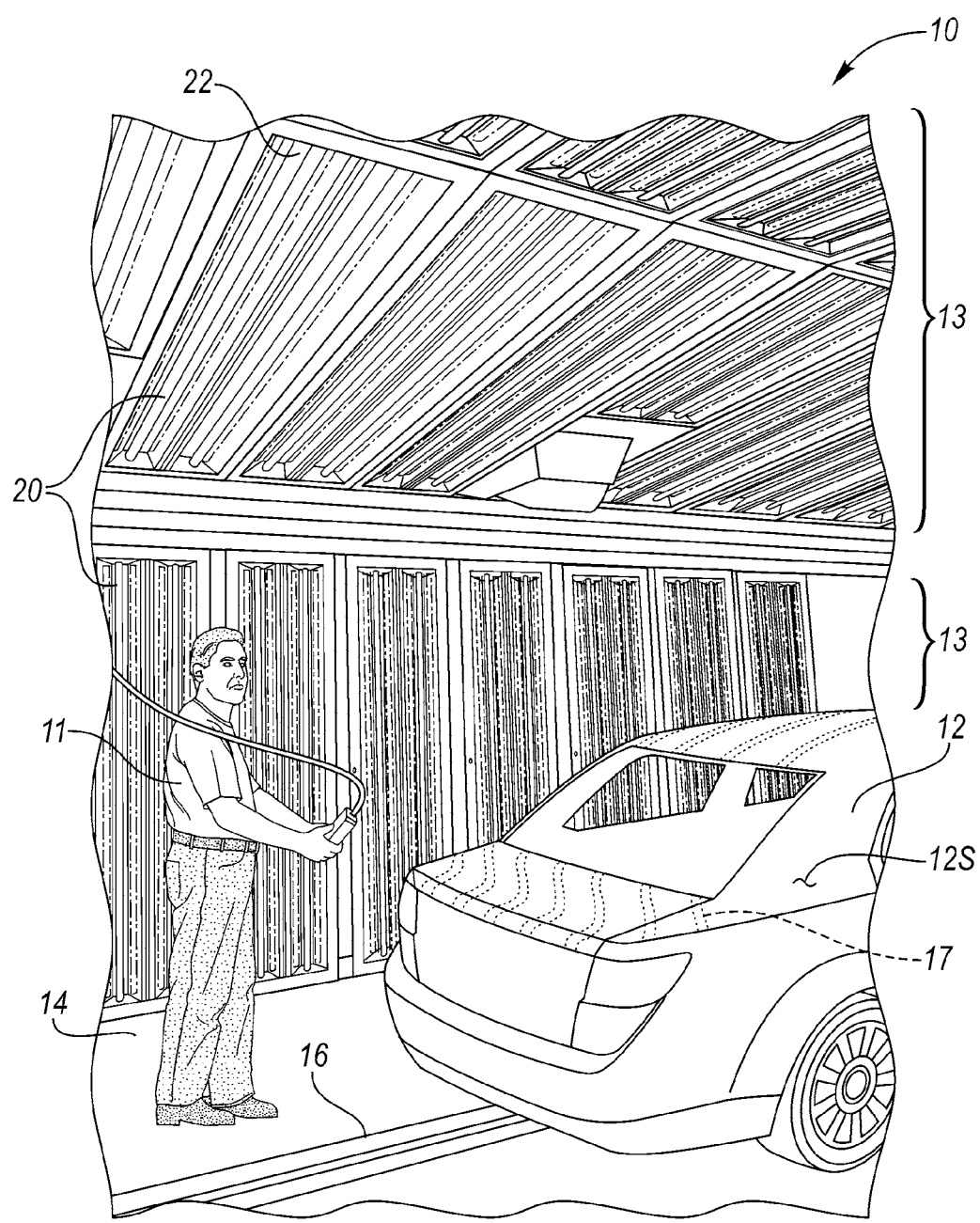
FIG. 1 is a schematic perspective view illustration of an example manual paint inspection line that is illuminated in accordance with the presently disclosed method.

Referring to the drawings, wherein like reference numbers refer to the same or similar components throughout the several views, an example manual inspection line 10 includes a component 12 having a painted surface 12S. The component 12 may be an automotive body as shown, a panel, or any other painted object having the painted surface 12S whose surface finish it may be desirable to inspect for topographic defects. While an automotive application is shown in FIG. 1, the manual inspection line 10 may be used for the inspection of any component 12 having such a painted surface 12S. The inspection line 10 may include a floor 14 with a conveyor 16, e.g., one or more rails or tracks suitable for transporting the component 12 to and from the manual inspection line 10. The conveyor 16 may be positioned overhead in an alternative embodiment provided that the position of the conveyor 16 does not interfere with lighting of the component 12.

The manual inspection line 10 includes at least one array 13 of light emitting diode (LED)-based lighting fixtures 20. Each LED-based lighting fixture 20 includes a pair of LED tubes 22, e.g., of the T5, T8, or T12 conventional tube sizes. The LED tubes 22 may be four feet in length to match conventional fluorescent tube lengths, or the LED tubes 22 may be any other application-suitable length. Depending on the application, the array(s) 13 may be fixed with respect to the walls and ceiling of a facility housing the manual inspection line 10.

While the exact alignment and orientation of the various LED-based lighting fixtures 20 may vary, the example manual inspection line 10 of FIG. 1 includes vertically-oriented LED-based lighting fixtures 20 positioned laterally with respect to the component, i.e., flanking the component 12. The manual inspection line 10 may also include angled, substantially horizontally-aligned LED-based lighting fixtures 20 spanning the component 12 from overhead. In an embodiment, the painted surface 12S may be irradiated with light at 200 foot-candles from the horizontally-aligned LED-based lighting fixtures 20 spanning the component 12 and at 150 foot-candles from the vertically-aligned LED-based lighting fixtures 20 flanking the component 12. The number and orientation of the lighting fixtures 20 should be sufficient to project one or more striped patterns 17 of light onto the component 12, i.e., the "zebra striping" described above, such that an inspector 11 may view the striped pattern(s) 17 of light to facilitate annual inspection of the painted surface 12S.

Figure 2:
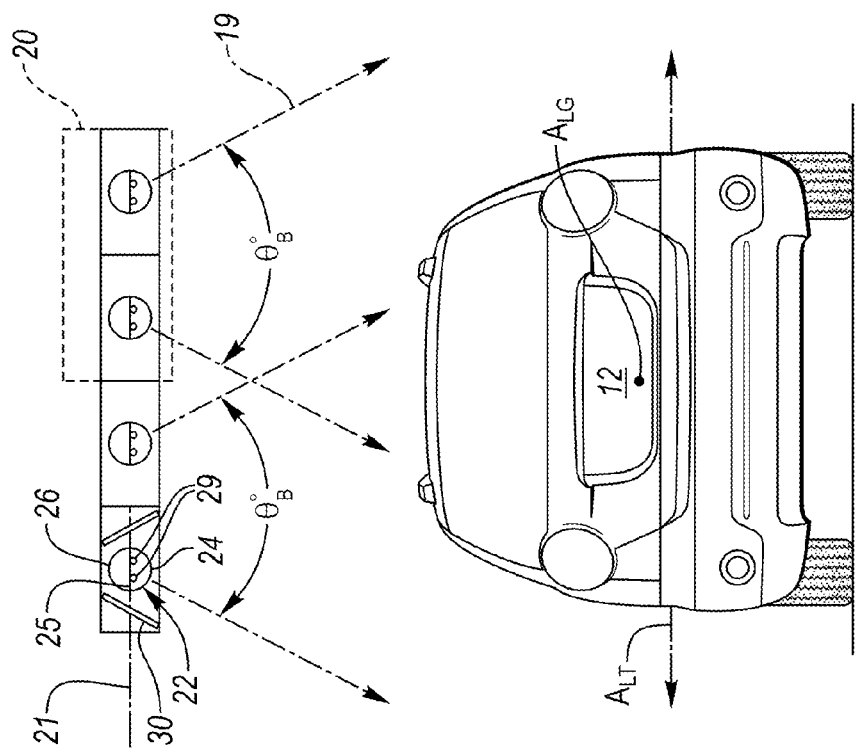
FIG. 2 is a schematic side view illustration of an example light emitting diode (LED)-based lighting fixture usable as part of the present method.

Referring to FIG. 2, the component 12 is shown schematically as a vehicle body as it appears with respect to a pair of example LED-based lighting fixtures 20. The LED-based lighting fixtures 20 are aligned such that they are parallel to a lateral axis $A_{LT}$ of the component 12 and orthogonal with respect to a longitudinal axis $A_{LG}$ of the component 12. However, the LED-based lighting fixtures 20 may be positioned at an angle with respect to the axes $A_{LT}$, $A_{LG}$, e.g., at 15-30 degrees with respect to the longitudinal axis $A_{LG}$. Light (arrows 19) emanates from the LED tubes 22 at a calibrated beam angle ($\theta°_B$) of at least 120 degrees and a color rendering index or CRI of at least 90 to thereby project the striped pattern 17 of light as best shown in FIG. 1 directly onto the painted surface 12S.

Each LED-based lighting fixture 20 includes two LED tubes 22 in parallel with each other, with each LED tube 22 positioned between a set of polished reflectors 30 as shown, e.g., polished aluminum mirrors or parabolic reflectors arranged at an angle of approximately 45 degrees to the horizontal. Other angles may be envisioned within the intended inventive scope provided the light (arrows 19) meets the lighting parameters set forth herein.

As noted above, conventional off-the-shelf LED replacement tubes tend to provide a less than satisfactory beam angle, CRI, and color temperature combination. Individual replacement tubes may exist that provide some unconventional lighting parameters such as a high CRI or beam angle. However, in the present approach the LED-based lighting fixtures 20 must provide all of the required lighting parameters set forth below.

In order to provide the required set of lighting parameters, each LED tube 22 may include a printed circuit board assembly (PCBA) 26 and an arcuate diffuser panel 24. The diffuser panel 24 may be snap fit or otherwise connected to the PCBA 26 to form an annular tube as shown, e.g., a retrofit T5, T8, or T12 tube for replacing existing fluorescent tubes. Alternatively, the diffuser panel 24 may be integrally formed with the PCBA 26 such as in the example of a board-mounted diffuser panel 24 being directly to the PCBA 24, in which case the shape of the diffuser panel 24 may be annular or non-annular, e.g., square or rectangular.

The PCBA 26 also includes a horizontal surface 25 having a plurality of LEDs 29. To achieve the required beam angle ($\theta°_B$) of at least 120 degrees, over 210 degrees in another embodiment, or over 300 degrees in yet another embodiment, the individual LEDs 29 of the PCBA 26 may be staggered and/or angled with respect to the horizontal surface 25, or in other words with respect to a plane 21 of the PCBA 26. The materials of the diffuser panel 24 may also be configured to provide an opacity level sufficient for obscuring the profiles of the individual LEDs 29 from view by the inspector 11.

That is, for optimal inspection of the painted surface 12S of FIG. 1 the profile or outline of the individual LEDs 29 of the PCBA 26 shown in FIG. 2 should not be visible to the inspector 11 of FIG. 1 from the outside of the diffuser panel 24, a problem often found in conventional off-the-shelf LED tubes that can render such light tubes inoperable for use in an inspection process. Instead, light from all of the LEDs 29 used in the LED tube 22 should be substantially diffused by the diffuser panel 24 so as to provide substantially uniform and homogenous lighting along the entire length of the LED tube 22. For example, the intensity of light as measured in close proximity to a given LED 29 from directly outside of the diffuser panel 24 should not vary by more than 10-20 percent from light measured anywhere else along a length of the LED tube 22. Such a standard may help to provide the proper level of opacity of the diffuser panel 24 for paint inspection purposes.

Figure 3:
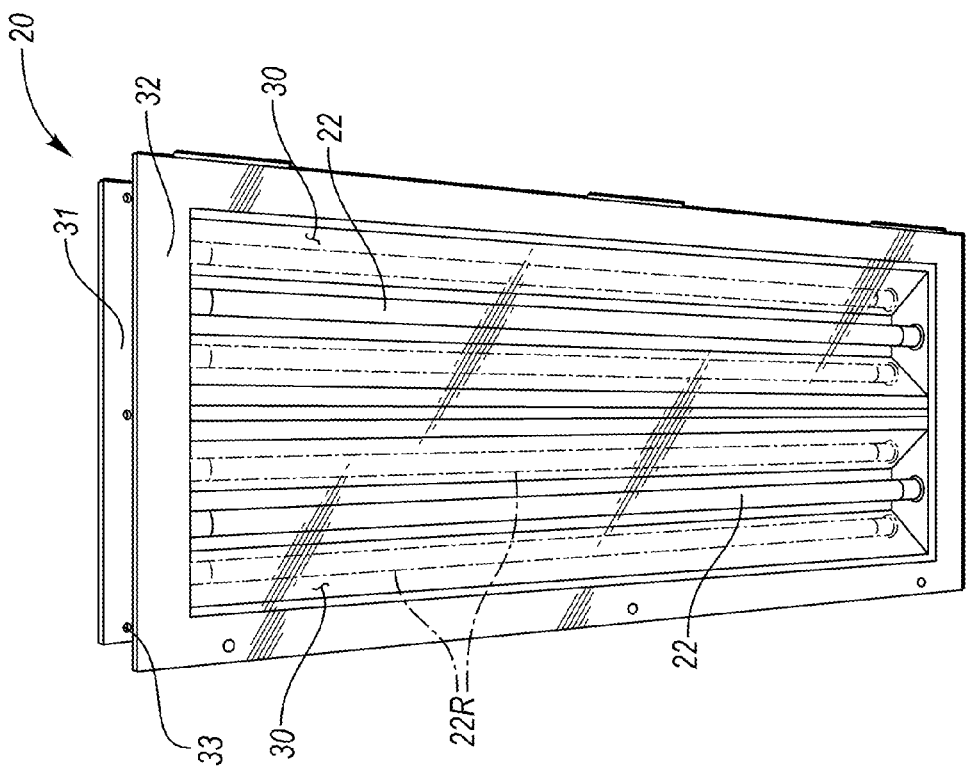
FIG. 3 is a schematic plan view illustration of the example lighting fixture shown in FIG. 2.

FIG. 3 is a schematic illustration of an example LED-based lighting fixture 20. Such an LED-based lighting fixture 20 may include a housing 32, which as shown is a conventional rectangular box of sheet metal having an end flange 31 with a set of mounting holes 33. The LED-based lighting fixture 20 may be mounted to a ceiling or wall of a facility housing the manual inspection line 10 shown in FIG. 1 via threaded bolts or other fasteners. As shown, each LED-based lighting fixture 20 has two parallel LED tubes 22 and four polished reflectors 30, such that when electrical power is delivered to the LED-based lighting fixture 20 via, for instance, a 100-277 volt LED driver (not shown), four reflected images 22R of the energized LED tubes 22, modified as set forth above, are projected onto the painted surface 12S of FIGS. 1 and 2 along with direct reflections of the LED tubes 22 themselves. This ultimately produces the six stripes of the striped pattern 17 shown in FIG. 1. While the angles of the polished reflectors 30 are about 45 degrees in a conventional lighting fixture, and may be the same here, other angles may be contemplated to help achieve the required beam angle of the present method 100.

Figure 4:
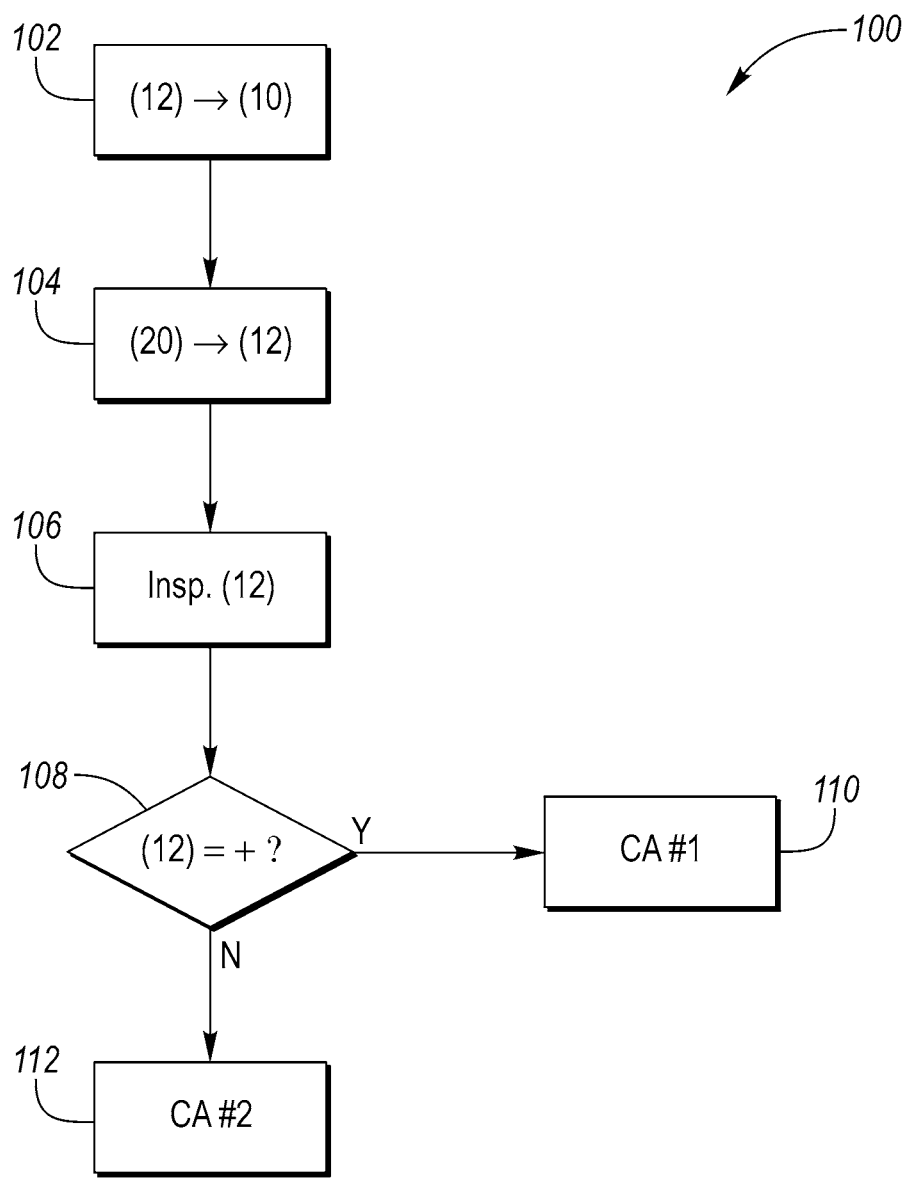
FIG. 4 is a flow chart describing an example LED-based method for inspecting a painted finish for topographic defects.

Referring to FIG. 4, an example embodiment of the inspection method 100 begins with step 102. Step 102 includes positioning a component having a painted surface, for instance the component 12 and the painted surface 12S of FIG. 1, with respect to an array 13 of lighting fixtures 20 of the type described above. Step 102 may include transporting a vehicle body or a vehicle panel via the conveyor 16 of FIG. 1 in a possible embodiment. The method 100 proceeds to step 104 once the component 12 is properly positioned with respect to the array 13.

At step 104, the method 100 includes illuminating the positioned component 12 via the array 13. Illuminating the component 12 includes irradiating the painted surface 12S of the component 12 with the striped pattern 17 of the light (arrows 19), as shown in FIG. 1, at a beam angle of at least 120 degrees and with a CRI of at least 85 or at least 90 in possible embodiments. For instance, light (arrows 19 of FIG. 2) from two LED tubes 22 per lighting fixture 20 may be reflected via the reflectors 30 shown schematically in FIGS. 2 and 3 to generate the "zebra striping" noted above, i.e., the six stripes of light on the painted surface 12S. In another embodiment, irradiating the painted surface 12S occurs at a beam angle of at least 210 degrees. The CRI may be in the range of between 90 and 93 in another embodiment. A desirable color temperature of light for inspection in the above embodiments is about 5000° K. However, the method 100 is not necessarily limited to this particular color temperature. The method 100 then proceeds to step 106.

At step 106, the method 100 further includes inspecting the painted surface 12S for topographic defects while illuminating the component 12 with the light (arrows 19) from the array 13 shown in FIG. 1. As part of step 106, the inspector 11 of FIG. 1 may visually inspect the painted surface 12S for defects in the usual manner, and/or the inspector 11 may use automated inspection tools such as optical/machine vision systems to inspect the painted surface 12S for such defects.

Step 108 entails determining whether the component 12 has a finish that is acceptable relative to a calibrated standard. For example, the inspector 11 of FIG. 1 may determine if the component 12 contains more than a threshold number and/or size of topographic defects, either for the component 12 as a whole or for a designated area of the component 12. The method 100 proceeds to step 110 if fewer than the threshold number and/or size of topographic defects are detected, and to step 112 if the component 12 contains more than a threshold number and/or size of topographic defects.

Step 110 may include executing a first control action such as passing the component 12 onto the next step or stage in the manufacturing process. Step 110 may include recording a barcode or serial number of the component 12 in memory of a host machine or computer device (not shown) to verify the passing status of the component 12. Method 100 commences anew for the next inspected component 12.

Step 112 may include executing a second control action such as directing the component 12 into a rework or scrap stage in the manufacturing process, with the actual control step depending on the severity of the detected topographic flaws. Step 112 may include recording the barcode or serial number of the component 12 in memory of a computer device (not shown) to verify the failing status of the component 12. The method 100 commences anew for the next inspected component 12.

While the best modes for carrying out the invention have been described in detail, those familiar with the art to which this invention relates will recognize various alternative designs and embodiments for practicing the invention within the scope of the appended claims.

The invention claimed is:

1. A method of inspecting a surface finish of a component, the method comprising:
   positioning the component with respect to an array of light emitting diode (LED) lighting fixtures each having parallel LED tubes and a plurality of reflectors arranged at an angle of approximately 45 degrees relative to horizontal;
   generating light via the array with a predetermined set of lighting characteristics, including a striped pattern, a beam angle of at least 120 degrees, a color rendering index of at least 85, and a color temperature of about 5000 degrees Kelvin;
   illuminating the component with the generated light from the array, including reflecting light from the parallel LED tubes from the reflectors to generate six stripes of light per LED lighting fixture;
   inspecting the surface finish of the component for defects while illuminating the component with the generated light from the array; and
   executing a control action with respect to the component when the component contains at least one of a threshold number and a threshold size of the defects.

2. The method of claim 1, wherein generating light via the array includes providing the beam angle in a range of between 210 and 360 degrees.

3. The method of claim 1, wherein generating light via the array includes generating light with the color rendering index of at least 90.

4. The method of claim 1, wherein positioning the component with respect to an array of LED lighting fixtures includes positioning one of a vehicle body and a vehicle body panel with respect to the array.

5. The method of claim 4, wherein positioning one of a vehicle body and a vehicle panel with respect to the array includes positioning the vehicle body or the vehicle panel with respect to a plurality of horizontally-aligned LED lighting fixtures and a plurality of vertically-aligned LED lighting fixtures.

6. A method of inspecting a painted surface finish of a vehicle body, the method comprising:
   positioning the vehicle body with respect to an array of LED lighting fixtures each having two parallel LED tubes and four reflectors arranged at an angle of approximately 45 degrees relative to horizontal;
   generating light via the array with a predetermined set of lighting characteristics, including a striped pattern of exactly six stripes per LED lighting fixture, a beam angle of over 300 degrees, a color rendering index in the range of greater than 90, and a color temperature of 5000 degrees Kelvin (° K);
   illuminating the painted surface finish with the generated light from the array, including reflecting light from the parallel LED tubes using the four reflectors to generate six stripes of light per LED lighting fixture;
   inspecting the painted surface finish for defects while illuminating the component with the light from the array; and
   executing a control action with respect to the component when the component contains at least one of a threshold number and a threshold size of the defects.

7. The method of claim 6, wherein positioning the vehicle body with respect to an array of LED lighting fixtures includes positioning the vehicle body with respect to a plurality of horizontally-aligned LED fixtures spanning a longitudinal axis of the vehicle body and a plurality of vertically-aligned LED lighting fixtures flanking the longitudinal axis of the vehicle body.

* * * * *